United States Patent [19]

Ceisel et al.

[11] Patent Number: 4,941,895
[45] Date of Patent: Jul. 17, 1990

[54] PROCESS FOR THE CONTINUOUS SEPARATION OF MALEIC ANHYDRIDE FROM PROCESS GASES

[75] Inventors: Stephen C. Ceisel; James F. Conrad, both of Shorewood; Elizabeth M. Lestan, Joliet, all of Ill.; Allen P. Nelson, Munster, Ind.

[73] Assignee: Amoco Corporation, Chicago, Ill.

[21] Appl. No.: 397,392

[22] Filed: Aug. 23, 1989

[51] Int. Cl.$^5$ .......................................... C07D 307/60
[52] U.S. Cl. ....................................... 55/84; 55/82; 55/83; 549/256; 549/257; 549/258; 549/262
[58] Field of Search ............... 549/262, 256, 258, 257; 55/82, 83, 84

[56] References Cited

U.S. PATENT DOCUMENTS

| | | | |
|---|---|---|---|
| 2,583,013 | 1/1952 | Patterson | 55/82 |
| 2,951,555 | 9/1960 | Cooper | 55/82 |
| 3,024,251 | 3/1962 | Feder et al. | 549/262 |
| 3,149,935 | 9/1964 | Jamison et al. | 55/84 |
| 3,818,680 | 6/1974 | Marquis | 549/262 |
| 4,352,755 | 10/1982 | Higgins et al. | 549/258 |

FOREIGN PATENT DOCUMENTS 3138861  5/1982  Fed. Rep. of Germany .......... 55/82

*Primary Examiner*—Mary C. Lee
*Assistant Examiner*—Bernard I. Dentz
*Attorney, Agent, or Firm*—Gunar J. Blumberg; William H. Magidson; Ralph C. Medhurst

[57] ABSTRACT

A process is disclosed for increasing the recovery of maleic anhydride from the product condenser. Maleic anhydride is added to the oxidation reactor gaseous effluent. Maleic acid buildup in the condenser is reduced; condenser plugging is reduced; and process run time required to build up to production rates after periodic cleaning can be reduced.

5 Claims, No Drawings

PROCESS FOR THE CONTINUOUS SEPARATION OF MALEIC ANHYDRIDE FROM PROCESS GASES

FIELD OF THIS INVENTION

This invention relates to the product of maleic anhydride from the process gases fron the catalytic oxidation of a hydrocarbon in the vapor phase.

BACKGROUND OF THE INVENTION

Maleic anhydride is of significant commercial interest throughout the world. It is used alone or in combination with other acids in the manufacture of alkyl and polyester resins. It is also a versatile intermediate for chemical synthesis. Significant quantities of maleic anhydride are produced each year to satisfy these needs.

Maleic anhydride has been produced by the catalytic oxidation in the vapor phase of n-butane, butene and other $C_4$ fractions and benzol (i.e., benzene). Typical processes for production of maleic anhydride are taught in U.S. Pat. Nos. 4,052,417; 4,065,468; 4,089,870; 4,097,501; 4,143,056; 4,244,879; 4,392,986; 4,448,978; 4,562,228; 4,567,158; 4,596,878; 4,675,420; amoung others. Products of the oxidation are maleic anhydride, water, carbon dioxide and other by-products.

In the usual vapor-phase oxidation of an appropriate hydrocarbon to prepare maleic anhydride, the effluent product stream from the oxidation unit ordinarily contains from about ½ to about 2.5 volume percent of maleic anhydride, from 2 to 6 volume percent water and other components such as carbon dioxide, carbon monoxide, and unconverted hydrocarbon. The major components of this product gas stream are nitrogen and oxygen.

Conventionally, the gas stream from the oxidation is first cooled to condense about one-half of the maleic anhydride and then, after separating the condensate, scrubbing the gas stream to recover the remaining maleic anhydride.

According to known methods, the maleic anhydride is obtained from the process gases in the following manner. First, the gases are cooled to a temperture of about 55° to 65° C. Such tempertures lies above the so-called thaw point of maleic anhydride. In the butame process approximately 40 to 45 percent of the maleic anhydride can be condensed from the process gases. The lower the condensation temperture which is chosen, the more the water contained in the gas will be bound by the condensing maleic anhydride, thus forming maleic acid. However, the formation of maleic acid is undesirable, since the maleic acid is a solid product and is poorly soluble in molten maleic anhydride. Such leads to fouling of the condenser and plugging up of the downstream apparatus, which in turn, results in the loss of throughput and yield.

SUMMARY OF THE INVENTION

It has been found that injecting maleic anhydride of a minimum melting point of 52.5° C. into the reactor effluent stream before the maleic anhydride gaseous stream enters the condenser increases the recovery of maleic anhydride from 40–45 wt. % to about 50–60 wt. %, reduces the rate of fouling due to maleic acid buildup on the condenser surface and consequent condenser plugging, and can reduce process time required to build up production rates after periodic cleaning of the condenser to remove maleic acid buildup. The maleic anhydride is injected into the gas stream wherein the gas stream is at a temperature of from about 200° F. to about 350° F. to create a gas phase of the injected maleic anhydride.

DETAILS OF THE INVENTION

The invention disclosed herein is concerned with the addition of pure maleic anhydride (MAN) to the reactor effluent stream entering the partial condenser in a maleic anhydride process. MAN from this effluent stream is partially condensed in a single-pass U-tube heat exchanger prior to entering a scrubber. Injection of pure MAN into the feed stream to the U-tube condenser promotes better heat mass transfer so that a larger portion of the product is condensed. This increase in efficiency of the heat exchanger results in an increase in production capability of the unit, as well as a decrease in production costs due to energy saved by not having to process the material through the recovery train of the unit.

Followinng is a brief desccription of the maleic anhydride process. A process stream from the reactors, containing MAN, air, unprocessed butane, and by-products of oxidation, is passed through coolers to lower the stream temperature to 200°–350° F. The stream then passes through a U-tube heat exchanger, or partial condenser, where a portion of the MAN condenses out of the stream and is collected at the bottom of the exchanger. The percentage of MAN removed from the process stream is referred to as the knockout rate. The MAN which does not condense from the gas stream must be processed through a scrubber, dehydrator and a splitter (collectively referred to as the back end) before being combined with the MAN which was previously knocked out in the partial condenser. This processing of MAN throughout the back end requires a considerable amount of capital and energy, as well as a decrease in the overall process yield. The total production capability of a particular unit may be governed by the performance of the partial condenser since the back end is the limiting factor in this process.

The partial condenser has a typical run time of three to four months. Upon start up after a wash, the partial condenser operates at low knock out rates for approximately two weeks due to an excessive heat transfer rate. After the tubes are partially fouled by a film of maleic acid (MA) and MAN, a maximum knock out rate of 40–45% is achieved and maintained for the duration of the run time. Eventually, so much maleic acid is plated out on the tubes that the heat transfer rate becomes insufficient and the knock out rate drops rapidly, indicating that washing is required.

By increasing the amount of MAN in the incoming stream, two advantages are realized. Addition of MAN will promote a more rapid coating of the U-tubes, thereby shortening the duration of the initial low knock out rate period. Continued injection then provides a higher MAN to MA ratio, thereby causing any MA which has plated out on the U-tubes to be redissolbed into the MAN which condensed on the tubes. This is a method of self-cleaning which is expected to extend the run time. Also, higher knock out rates of 50–60% (as opposed to typical rates of 40–45%) have been maintained during recent experiments, thereby reducing the amount of material which must be processed through the back end. An economic advantage is realized through a reduction in the percentage of material which must be processed through the back end. This economic advantage can be used to either increase the capacity of an existing facility or decrease the capital requirements of a new one.

In the operation of the condenser, it has been found that if the fouling of the condenser results in a concentration of maleic acid of over 3 to 5 wt. % in the maleic anhydride on the condenser tubes, the rate of fouling of the condenser increases rapidly. On the other hand, if the concentration of maleic acid is maintained below the critical concentration of 3–5 wt. % in the coating of maleic anhydride on the condenser tubes, the rate of fouling increase is negligible.

Suprisingly, it has been found that injection of liquid, highly-pure maleic anhydride into the reactor effluent stream entering the condenser serves to prevent the buildup of the concentration of maliec acid in the coating on the condenser tubes. Injection of the maleic anhydride into the reactor effluent stream can be in the form of a liquid spray to form a vapor or in the form of a vapor. Either physical form is suitable. However, it is essential that the injected maleic anhydride is in the vapor phase after injection.

In one embodiment, the highly-pure maleic anhydride, of a minimum melting point of at least 52.5° C. is injected into the reactor effluent gas stream by means of a fogging-jet spray nozzle. It is essential that the nozzle create a fogging spray. A suitable fogging-jet atomizing spray nozzle is Fog Jet (trademark), 7N nozzle, Spraying Systems Company, Wheaton, Illinois 60187, which atomizes a liquid to a shower-like spray pattern of very fine droplets.

It is essential that the purity of the maleic anhydride injected into the gas stream be of the highest. It is essential that content of maleic acid be at a minimum, that maleic anhydride content preferably be 99.9 wt. %. Injection of crude maleic anhydride containing maleic acid in amounts greater than 2 wt. % of the maleic anhydride content is unsuitable. The presence of maleic acid in amounts greater than about 2 wt. % increases the rate of fouling of the condenser tubes.

Although the mechanism is not known by which the instant invention operates to control the concentration of maleic acid in the maleic anhydride coating on the surface of the condenser tubes, it is theorized that a partial scouring action occurs on the surface of the tubes caused by the relative equilibrium concentrations of the maleic anhydride, water and maleic acid in the reactor effluent stream.

Addition of maleic anhydride to the reactor effluent stream should be at least 1 wt. % of the maleic anhydride content of the effluent stream. Maximum addition of maleic anhydride in limited only by the capacity of the downstream equipment to recover the added maleic anhydride and the economics of recycling highly purified maleic anhydride.

In one embodiment of the invention a plant run was made over a period of 58 days during which maleic anhydride, M.P. 52.5° C., 99.9 wt. % pure, was injected into the reactor effluent steam containing maleic anhydride, water, and by-product inpurities. Injection was by means of an atomizing spray nozzle. The amount of maleic anhydride injected was about 10 wt. % of the maleic anhydride present in the effluent stream. A control run over a period of 18 days had been made previously in the same plant during which the condensation recovery rate in the condenser had averaged approximately 30 wt. % of the maleic anhydride present. Upon addition of the maleic anhydride, the condensation recovery rate increased to between 50 to 60 wt. % of the maleic anhydride present and remained at that level for the period of 58 days.

Accordingly, the instant invention comprises a process for recovery of maleic anhydride from a gaseous mixture containing maleic anhydride which comprises contacting said mixture with maleic anhydride in a gas phase wherein said maleic anhydride in injected into a gas stream effluent from an oxidation reactor, said gas stream effluent is at a termperature of from about 200° F. to about 350° F., and maleic anhydride is recovered in a condenser. The maleic anhydride injected into said reactor effluent gas stream is at least 1 wt. % of the maleic anhydride of said reactor effluent gas stream. The maleic anhydride injected into said reactor effluent gas stream can be in liquid phase and is injected into said reactor effluent gas stream by means of an atomizing spray nozzle. The maleic anhydride injected into said reactor effluent gas stream preferably has a melting point of 52.5° C. The maleic anhydride injected into said reactor effluent gas stream preferably contains less than 2 wt. % maleic acid.

That which is claimed is:

1. A process for recovery of maleic anhydride from a gaseous mixture of a reactor effluent gas stream containing maleic anhydride which comprises contacting said mixture with maleic anhydride in a gas phase wherein said maleic anhydride is injected into a gas stream effluent from an oxidation reactor, said gas stream effluent is at a temperature of from about 200° F. to about 350° F., and maleic anhydride is recovered in a condenser.

2. The process of claim 1 wherein maleic anhydride injected into said gas stream is at least 1 wt. % of the maleic anhydride content of said reactor effluent gas stream.

3. The process of claim 1 wherein said maleic anhydride injected into said gas stream is a liquid and is injected into said gas stream by means of an atomizing spray nozzle.

4. The process of claim 1 wherein said maleic anhydride injected into said reactor gas stream has a M.P. of at least 52.5° C.

5. The process of claim 1 wherein said maleic anhydride injected into said gas stream contains less than 2 wt. % maleic acid.

* * * * *

UNITED STATES PATENT OFFICE
CERTIFICATE OF CORRECTION

Patent No. 4,941,895　　　　　　　　　　Dated July 17, 1990

Inventor(s) Stephen G. Ceisel, James F. Conrad, Elizabeth M. Lestan & Allen P. Nelson It is certified that error appears in the above-identified patent and that said Letters Patent is hereby corrected as shown below:

| Col. | Line | |
|---|---|---|
| 1 | 8 | "gases fron" should read --gases from-- |
| 1 | 24 | "amoung" should read --among-- |
| 1 | 43 | "tempertures" should read --temperature-- |
| 2 | 13 | "heat mass" should read --heat and mass-- |
| 2 | 59 | "redissolbed" should read --redissolved-- |
| 3 | 5 | "condenser results" should read --condenser tubes results-- |

Signed and Sealed this

Seventeenth Day of September, 1991

Attest:

HARRY F. MANBECK, JR.

Attesting Officer　　　　Commissioner of Patents and Trademarks